US00PP26021P3

(12) United States Plant Patent
Nir

(10) Patent No.: US PP26,021 P3
(45) Date of Patent: Oct. 27, 2015

(54) ***CHAMELAUCIUM* PLANT NAMED 'UMBRELLA'**

(50) Latin Name: *Chamelaucium uncinatum*
Varietal Denomination: UMBRELLA

(71) Applicant: Nitzan Nir, Kfar Hess (IL)

(72) Inventor: Nitzan Nir, Kfar Hess (IL)

( * ) Notice: Subject to any disclaimer, the term of this patent is extended or adjusted under 35 U.S.C. 154(b) by 106 days.

(21) Appl. No.: 13/986,493

(22) Filed: May 7, 2013

(65) Prior Publication Data

US 2014/0338080 P1 Nov. 13, 2014

(51) Int. Cl.
*A01H 5/02* (2006.01)

(52) U.S. Cl.
USPC ..... Plt./229
CPC ..... *A01H 5/02* (2013.01)

(58) Field of Classification Search
USPC ..... Plt./229
See application file for complete search history.

(56) References Cited

PUBLICATIONS

DEMEX Flowers 2012.*

* cited by examiner

*Primary Examiner* — Keith O. Robinson
(74) *Attorney, Agent, or Firm* — Cassandra Bright

(57) ABSTRACT

A new and distinct *Chamelaucium* cultivar named 'UMBRELLA' is disclosed, characterized by a large quantity of late blooming, medium sized, pink colored flowers. The new variety is a *Chamelaucium*, normally producing cut flower stems, or as a garden or container plant.

1 Drawing Sheet

Latin name of the genus and species: *Chamelaucium uncinatum.*

Variety denomination: 'UMBRELLA'.

BACKGROUND OF THE INVENTION

The new *Chamelaucium* cultivar is the product of a planned breeding program conducted by the inventor, Nitzan Nir, in Kfar Hess, Israel. The objective of the breeding program was to produce new *Chamelaucium* varieties for ornamental commercial applications. The new variety was selected as a hybrid seedling from the breeding program at a commercial nursery in Kfar Hess, Israel.

The seed parent is the unpatented variety referred to as *Chamelaucium uncinatum* 'Hot Pink'. The pollen parent is the unpatented, variety referred to as *Chamelaucium uncinatum* 'Early Violet'. The new variety was discovered in April of 2009 by the inventor in a group of seedlings resulting from previously mentioned crossing, in a commercial nursery in Kfar Hess, Israel.

Asexual reproduction of the new cultivar has been performed by vegetative cuttings. This was first performed at a commercial nursery in Kfar Hess, Israel in February of 2010 and has shown that the unique features of this cultivar are stable and reproduced true to type in successive generations.

SUMMARY OF THE INVENTION

The cultivar 'UMBRELLA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'UMBRELLA'. These characteristics in combination distinguish 'UMBRELLA' as a new and distinct *Chamelaucium* cultivar:

1. Late blooming season.
2. Unique pink flower.
3. Medium flower size.
4. Large quantity of flowers.

PARENT COMPARISON

Plants of the new cultivar 'UMBRELLA' are similar to plants of the seed parent, *Chamelaucium uncinatum* 'Hot Pink' in most horticultural characteristics, however, plants of the new cultivar 'UMBRELLA' bloom earlier, and produce flowers of a lighter pink color than the seed parent. 'UMBRELLA' also produces more flowers compared to the seed parent.

Plants of the new cultivar 'UMBRELLA' are similar to plants of the pollen parent; *Chamelaucium uncinatum* 'Early Violet' in most horticultural characteristics, however, plants of the new cultivar 'UMBRELLA' bloom earlier, and produce larger flowers of a medium pink color whereas the pollen parent produces flowers which are dark violet colored. 'UMBRELLA' also produces more flowers compared to the pollen parent.

COMMERCIAL COMPARISON

Plants of the new cultivar 'UMBRELLA' are comparable to the variety *Chamelaucium uncinatum* 'Wendy', unpatented. The two *Chamelaucium* varieties are similar in most horticultural characteristics; however, the new variety 'UMBRELLA' produces darker colored flowers, and more flowers and buds per plant.

Plants of the new cultivar 'UMBRELLA' can also be compared to the commercial variety *Chamelaucium uncinatum* 'Nir', unpatented. These varieties are similar in most horticultural characteristics; however 'UMBRELLA' flowers later, and produces a slightly smaller flower and more flowers and buds per plant.

BRIEF DESCRIPTION OF THE PHOTOGRAPH

The accompanying photograph in FIG. 1 illustrates in full color a close up of typical flowers and foliage of 'UMBRELLA' at approximately 1 year of age. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'UMBRELLA' plants grown outdoors in Kfar Hess, Israel. The growing temperature ranged from 15° C. to 35° C. during the day and from −2° C. to 35° C. during the night. General light conditions are bright, normal sunlight. Measurements and numerical values represent averages of typical plant types.

Botanical classification: *Chamelaucium uncinatum* 'UMBRELLA'.

Age of plant described: At least 2 months old from a rooted cutting.

Typical flowering stems harvested per plant: 120 during the course of the season.

Vase life of flowers: Two weeks.

PROPAGATION

Time to produce a rooted plantlet: 30 to 60 days at approximately 24° C.

Root description: Fibrous.

PLANT

Growth habit: Upright plant produces multiple stems from a pinch, or after harvesting stems.

Height: 200 cm.

Plant spread: 80 cm.

Growth rate: Rapid.

Branching characteristics: Moderate branching occurs after pinching.

Length of primary lateral branches: 60 cm on average.

Diameter of lateral branches: 0.5 cm.

Quantity of primary lateral branches: 120, these are the harvested flowering stems.

Characteristics of primary lateral branches:

- *Form*.—Round.
- *Diameter*.—0.5 cm.
- *Color*.—Near RHS Grey-Grown 199A.
- *Texture*.—Smooth.
- *Strength*.—Stems brittle.

Internode length: Range from 1.5 to 7 cm.

FOLIAGE

Leaf:

- *Arrangement*.—Opposite.
- *Quantity*.—Approximately 6 leaves, in the 10-15 cm section from the top of the branch.
- *Average length*.—1.0 cm.
- *Average width*.—0.1 cm.
- *Shape of blade*.—Needle.
- *Apex*.—Acute.
- *Base*.—Attenuate.
- *Margin*.—Entire.
- *Texture*.—Glabrous all surfaces.
- *Pubescence*.—None.
- *Aspect*.—Straight, occurring at approximately a 15 to 30 degree angle.
- *Color*.—Young foliage: Near RHS Yellow-Green 144A. Mature foliage: Near RHS Green 137C.
- *Venation*.—Indistinguishable from foliage.
- *Petiole*.—Not present.

FLOWER

Natural flowering season: Plants planted during April through October begin flowering March through April, without a juvenility period in Kfar Hess, Israel. Plants flower continuously under short day conditions.

Days to flowering from rooted cutting: Approximately 60 days.

Inflorescence type: Terminal Panicle.

Individual flower type: Single, rotate 5 petaled with a cone shaped hypanthium. Flowers outwardly facing.

Persistent or self-cleaning: Self-Cleaning.

Lastingness: Up to 14 days in a vase. Approximately 45 to 60 days on the plant.

Typical flowering stem length: Approximately 65 cm.

Bud:

- *Shape*.—Spherical.
- *Length*.—0.35 cm.
- *Diameter*.—0.35 cm.
- *Color*.—Near RHS Red-Purple 65B.

Inflorescence size:

- *Diameter*.—Average 18 cm.
- *Length*.—Average 20 cm.

Flower size:

- *Diameter*.—Average 1.5 cm.
- *Length*.—Average 0.7 cm.

Corolla:

- *Petals*.—Arrangement: Rotate, not overlapping. Length: Average 0.4 cm. Diameter: Average 0.4 cm. Quantity: 5. Texture: Smooth. Apex: Obtuse rounded. Base: Fused into a hypanthium.
- *Color*.—When opening: Upper surface: Near RHS Purple 75A. Lower surface: Near RHS Purple 75A. Fully opened: Upper surface: Near RHS Purple 75A. Lower surface: Near RHS Purple 75A. Aging: Upper surface: Near RHS Purple 75A. Lower surface: Near RHS Purple 75A.

Hypanthium:

- *Diameter*.—Average 0.6 cm.
- *Length*.—Average 0.2 cm.
- *Shape*.—Obconical.
- *Color*.—When opening: Inner surface: Near RHS Purple 75A, speckled Red 53A. Outer surface: Near RHS Purple 75A. Fully opened: Inner surface: Near RHS Purple 75A, speckled Red 53A. Outer surface: Near RHS Purple 75A. Aging: Inner surface: Near RHS Purple 75A, speckled Red 53A. Outer surface: Near RHS Purple 75A.

Calyx/sepals:

*Quantity per flower*.—Fused into a single, conical structure.

*Length*.—0.2 cm.

*Width*.—0.6 cm.

*Margin*.—Entire, incised approximately 1 mm.

*Texture*.—Smooth.

*Color*.—Near RHS Green 137C.

Peduncle: Peduncle consists of the plant stem.

Pedicel:

*Length*.—0.6 cm.

*Diameter*.—0.1 cm.

Fragrance: None.

REPRODUCTIVE ORGANS

Stamens:

*Number*.—10.

*Filament length*.—1 mm.

*Filament color*.—Near RHS Red-Purple 69B.

Anthers:

*Shape*.—Oval.

*Length*.—0.25-0.5 mm.

*Width*.—0.2 mm.

*Color*.—Near RHS Red-Purple 65D.

Pollen: Not observed to date.

Pistil:

*Number*.—1.

*Length*.—0.5 cm.

*Color*.—Near RHS White 155A.

*Style color*.—Near RHS Red-Purple 65D.

*Stigma*.—Shape: Round. Color: Near RHS Red-Purple 65D. Texture: Glabrous.

OTHER CHARACTERISTICS

Seeds and fruits: Single flower produces one fruit. When the fruit is fertile, it will produce 1 seed, occasionally 2 seeds. Fruit type is a nut, colored near Grey-Brown N199A, seed is unwinged colored approximately 1.5 mm, brown in color, too minute to accurately measure color with RHS chart.

Disease/pest resistance: Neither resistance nor susceptibility to the normal diseases and pests of *Chamelaucium* have been observed to date.

Temperature tolerance: From −2° C. to 35° C.

Drought tolerance: Very good tolerance for drought.

What is claimed is:

1. A new and distinct cultivar of *Chamelaucium* plant named ‘UMBRELLA’ as herein illustrated and described.

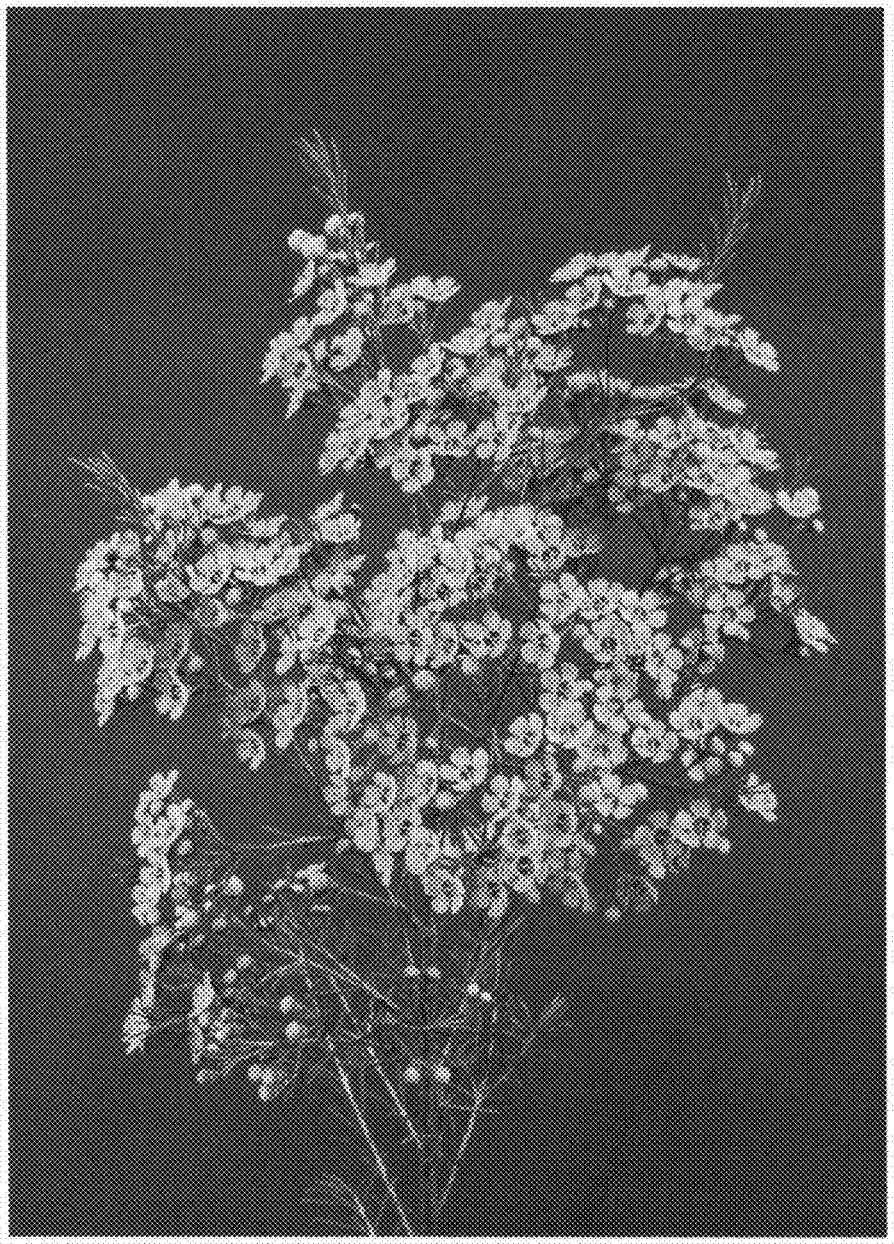

* * * * *